United States Patent [19]
Burke et al.

[11] Patent Number: 5,563,349
[45] Date of Patent: Oct. 8, 1996

[54] DIAMETRAL EXTENSOMETER

[75] Inventors: Andrew P. Burke, Marietta; David A. Graf, Woodstock; Joel R. Terry, Marietta, all of Ga.

[73] Assignee: Westinghouse Electric Corporation, Pittsburgh, Pa.

[21] Appl. No.: 282,445

[22] Filed: Jul. 29, 1994

[51] Int. Cl.⁶ ........................................ G01N 3/08
[52] U.S. Cl. ................................ 73/831; 73/760
[58] Field of Search ............... 73/778, 168, 862.391, 73/788, 774, 780, 826, 862.621, 818, 730, 760, 831, 856; 33/784, 787, 788

[56] References Cited

U.S. PATENT DOCUMENTS

| | | | |
|---|---|---|---|
| 3,630,071 | 12/1971 | Newhall | 73/4 D |
| 3,808,696 | 5/1974 | Possati | 33/178 |
| 3,898,885 | 8/1975 | Russell | 73/730 |
| 3,965,745 | 6/1976 | Carey | 73/730 |
| 4,286,470 | 9/1981 | Lynnworth | 73/861.18 |
| 4,507,871 | 4/1985 | Meyer et al. | 73/856 |
| 4,527,335 | 7/1985 | Meline | 33/787 |
| 4,597,184 | 7/1986 | Golinelli et al. | 33/501.1 |
| 4,607,531 | 8/1986 | Meline et al. | 73/794 |
| 4,714,803 | 1/1988 | Capelle et al. | 73/784 |
| 4,875,375 | 10/1989 | Wu et al. | 73/795 |
| 4,911,004 | 3/1990 | Leon | 73/168 |
| 4,930,228 | 6/1990 | Anderson et al. | 33/788 |
| 4,936,150 | 6/1990 | Burke et al. | 33/788 |
| 4,949,469 | 8/1990 | Wachtler | 33/702 |
| 5,123,283 | 6/1992 | Duff et al. | 73/760 |
| 5,148,612 | 9/1992 | Walser et al. | 33/784 |

FOREIGN PATENT DOCUMENTS 55-96432  7/1980  Japan ........................... 73/730

*Primary Examiner*—Richard Chilcot
*Assistant Examiner*—Max Noori
*Attorney, Agent, or Firm*—David G. Maire

[57] ABSTRACT

Disclosed is a diametral extensometer device useful for measuring diametral changes in a valve stem caused by axial loads on the valve stem used in a motor operated valve assembly. The device is useful in the field of valve diagnostics. The diametral extensometer is comprised of a semi-circular clamp member spaced from and partially surrounding the outer periphery of the valve stem. The clamp member has a reference pad that is adjustable radially with respect to the valve stem and a sensor pad having a sensor capable of measuring diametral changes in the valve stem and generating an electrical signal indicative of those changes. A stabilizer pad provides stability to the clamp member during installation of the clamp member and during movements of the valve stem. Non-stick surfaces are provided for smooth operation, and point contact with the valve stem eliminates errors associated with rocking of the traditional V-groove contacts. A two-piece clamp member having four points of contact with the valve stem may be used for improved accuracy. Quick disconnects may be used to join the two clamp members for nuclear or hazardous environment applications.

8 Claims, 3 Drawing Sheets

000000
DIAMETRAL EXTENSOMETER

BACKGROUND OF THE INVENTION

This invention relates to an improved device for measuring diametral changes in a cylindrical member. It relates particularly to a device, known as a diametral extensometer, for measuring slight diametral changes in a cylindrical member, such as a valve stem, that can be used for determining the axial loading on the cylindrical member.

In many industries, it is important to measure the variable dynamic axial loads that may be imposed on a cylindrical member or shaft. This is especially true in the nuclear power industry where remotely operable valves are used extensively and monitoring of the various operating parameters of the valves is required by the nuclear power regulating agencies.

It has been observed that one of the best ways to monitor the dynamic forces and events that occur during the operation of a valve is by measurement of the valve stem axial loads using either axial or diametral extensometers.

It is well known that one can calculate the axial load or stress in a valve stem, or any other similar member, by measuring changes in the diameter of the valve stem. The ratio of the diametral change to axial elongation, referred to as Poisson's ratio, is known and available for most materials. Therefore, by measuring the diametral changes in the valve stem using a device such as a diametral extensometer, axial strains and valve stem axial loads can be easily calculated and determined.

One such device described in U.S. Pat. No. 4,911,004 is designed as a clamp adapted to fit around an exposed portion of a valve stem or cylindrical member to measure diametral strains. Any diametral strains in the valve stem would cause the clamp to deflect. This deflection of the clamp was then measured and calibrated to indicate diametral and axial strains. The measurement of clamp deflection requires that the clamp be flexible enough to produce a reasonable level of output signals. However, such flexible clamps were often difficult to calibrate in order to produce linear measurements in response to the actual axial loads and strains in the valve stem. Such devices are difficult to set-up, calibrate and remove in a plant environment.

U.S. Pat. No. 5,123,283 describes a device which measures diametral strain directly, thus eliminating the problems associated with a flexible clamp device. Improved accuracy and simplicity of field assembly are, however, still desired for nuclear power plant applications.

SUMMARY OF THE INVENTION

It is therefore an object of this invention to provide a diametral extensometer device for determining diametral changes in a valve stem or other cylindrical member that is simple and easily installed on commercial motor operated valves and which provide precise, repeatable measurements.

It is another object of this invention to provide a diametral extensometer device for determining diametral changes in a valve stem or other cylindrical member that is able to provide direct and continuous measurement of the axial loads on a movable valve stem while the valve is in service.

These and other objects of this invention can be attained by a device for determining the diametral changes in a shaft produced by axial loads on said shaft, having a first clamp member adapted to be spaced from and to partially surround the outer periphery of the shaft; a first stabilizer pad springably attached to a first end of the first clamp member and adapted to be biased against the shaft; a second stabilizer pad springably attached to a second end of the first clamp member opposed the first stabilizer pad and adapted to be biased against the shaft; a reference pad fixably attached to the first clamp member between the first stabilizer pad and the second stabilizer pad and adapted to make contact with the shaft; a second clamp member attached to the first clamp member and adapted to be spaced from and to partially surround the outer periphery of the shaft; and a sensor pad springably attached to the second clamp member opposed the reference pad and adapted to be biased against the shaft; and means for sensing relative movement between the second clamp member and the sensor pad.

DETAILED DESCRIPTION OF THE INVENTION

Figure 1:
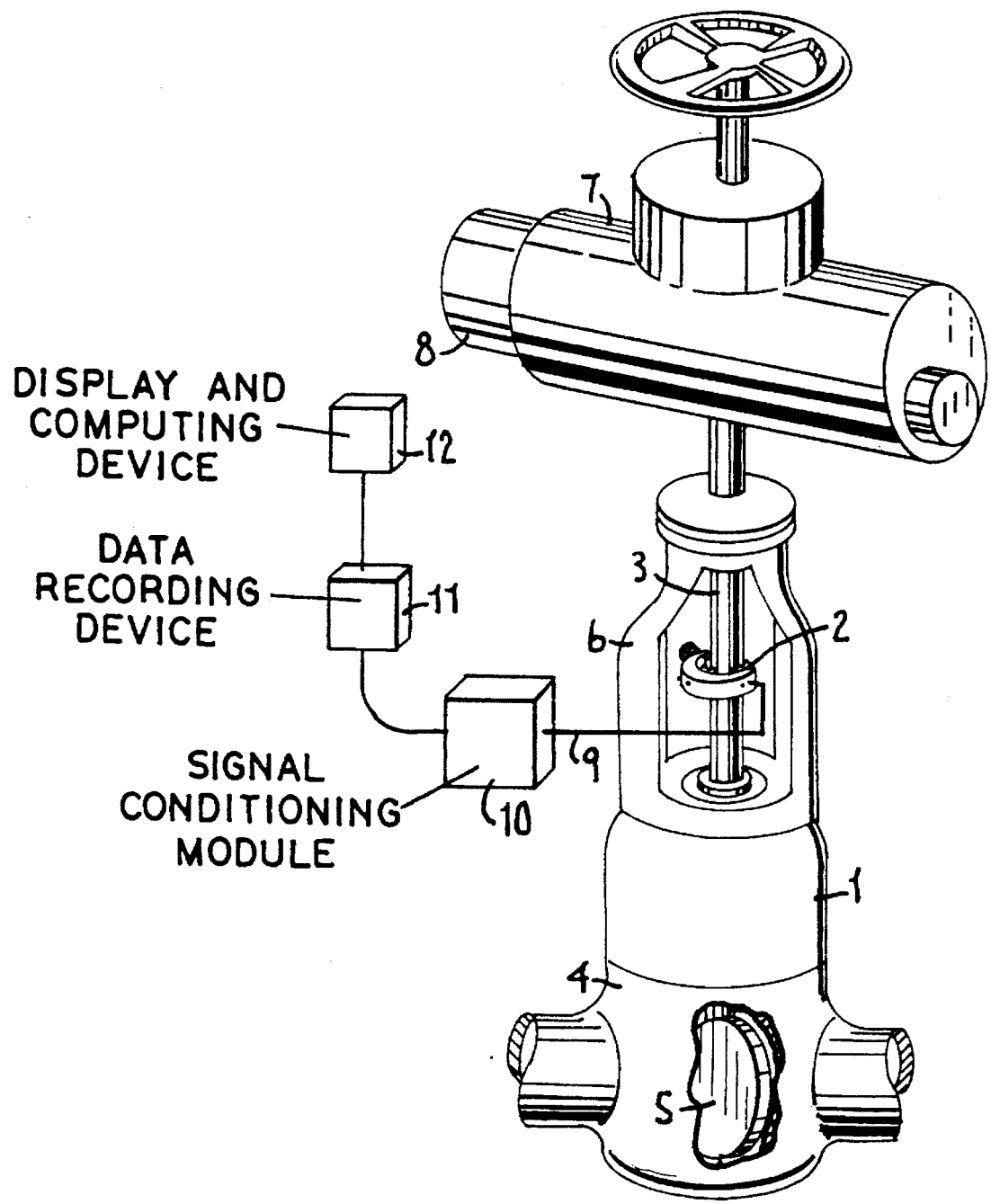
FIG. 1 is an isometric view of a typical motor operated valve assembly, partly in section to illustrate the installation and placement of the diametral extensometer device of this invention on the valve stem of the motor operated valve assembly.

FIG. 1 is an isometric view of a typical motor operated valve assembly 1, partly in section, to illustrate the installation and placement of the diametral extensometer device 2 of this invention on the cylindrical valve stem 3 of the valve assembly. The valve assembly 1, generally is comprised of a valve body 4 which contains a valve plug or gate 5, operated to a closed, open or intermediate position with respect to a valve seat within the valve body 4 by the valve stem 3. The valve stem is partially enclosed by a valve yoke 6 which supports a valve actuator 7 operated by an electric motor 8.

As shown in FIG. 1, the diametral extensometer device 2 of this invention is fastened around a portion of the outer periphery 16 of the cylindrical valve stem 3. The diametral extensometer 2 has an electrical cable 9 leading from the diametral extensometer 2 to an electrical signal conditioning module 10, a data recording device 11, such as a computer disk, and to a computing and display device 12, such as a personal computer.

Figure 2:
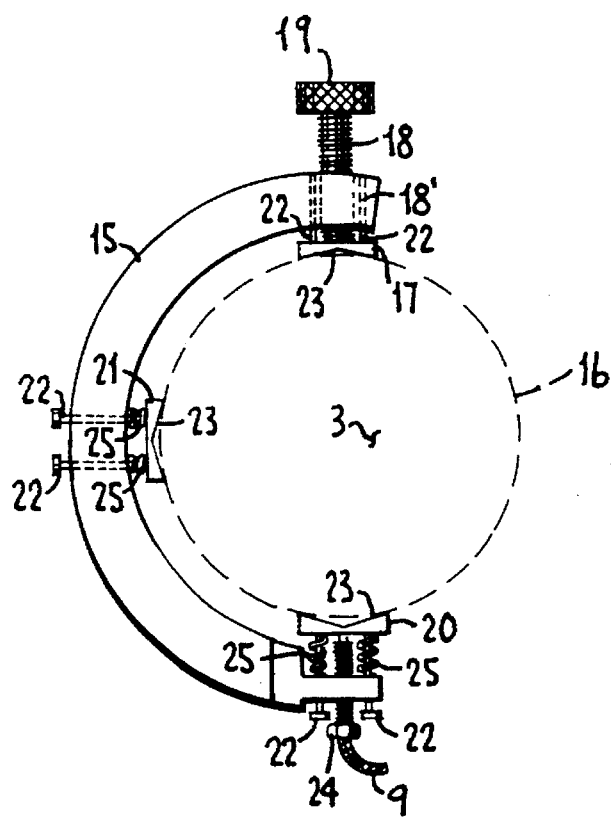
FIG. 2 is a top view, partly in section, illustrating an embodiment of the diametral extensometer device of this invention mounted on a cylindrical valve stem.
Figure 3:
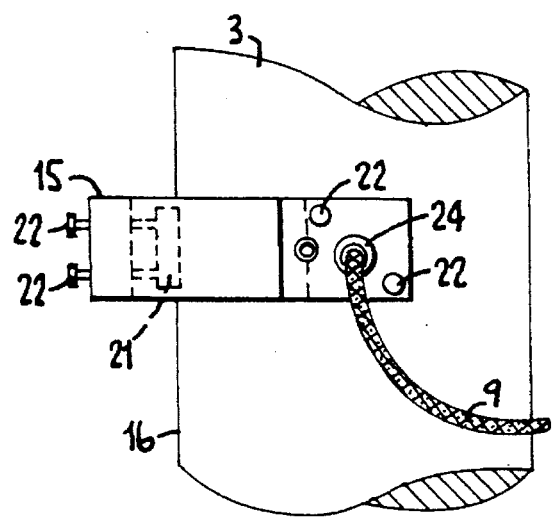
FIG. 3 is an elevational view illustrating the embodiment of the diametral extensometer device of FIG. 2 mounted on a cylindrical valve stem.

As shown in FIGS. 2 and 3, the diametral extensometer device of this invention may be comprised of a semi-circular clamp member 15 sized to fit in a spaced relationship slightly away from and partially surrounding the outer periphery 16 of the cylindrical valve stem 3 of the valve assembly 1. The semi-circular clamp member 15 is preferably made of metal, such as steel or brass, but could also be made of a rigid reinforced plastic to reduce its cost.

The semi-circular clamp member 15 has a reference pad 17 secured to one end thereof. The reference pad 17 may be adjusted radially with respect to the valve stem 3, by adjustment of the leading end of a threaded shaft 18 which contacts the back of the reference pad 17 and extends through a threaded opening 18' in the end of the semi-circular clamp member 15. Adjustment of the threaded shaft 18 and in turn the reference pad 17 is made using the adjustment knob 19 attached to the outer end of the threaded shaft 18. A spring loaded sensor pad 20 is secured to the other end of the semi-circular clamp member 15 and a spring loaded stabilizer pad 21 is secured to the semi-circular clamp member 15 substantially midway between the reference pad 17 and the sensor pad 20, as illustrated in FIG. 2. The pads 17, 20 and 21 may be attached to the semi-circular clamp member 15 by a pair of pins 22 that allow the pads 17, 20 and 21 to move in and out radially with respect to the valve stem 3. The sensor pad 20 and stabilizer pad 21 have springs 25 held captive by the pins 22 that allow for a constant pressure of the semi-circular clamp member 15 to the valve stem periphery 16 for the purpose of holding the clamp member 15 to the valve stem 3. The pads 17, 20 and 21 may have substantially V-shaped bearing surfaces 23 to engage portions of the periphery of the valve stem 3 and may be of the same dimensions. However, it has been found that a rocking motion of such V-shaped pads can introduce an error in the measurement of very small diametral movements if the pad is not squarely seated on the valve stem 3. This is especially true for a threaded valve stem. Therefore, it may be desirable in some applications to use a reference pad 17 and/or a sensor pad 20 which is adapted to make essentially point contact with the member being measured. Bearing surface 23 of stabilizer pad 21 may be a non-stick surface, such as Teflon or graphite impregnated metal or a plastic or other material with a low coefficient of friction. A non-stick surface is desirable in order to minimize friction between the valve stem 3 and the bearing surface 23 as the valve stem 3 changes diameter. Friction at this point may create forces which can affect the accuracy of the strain measurement at the sensor pad 20.

The reference pad 17 and the sensor pad 20 are preferably located opposed each other across the full diameter of the valve stem 3. By placing the sensor pad 20 and the reference pad 17 opposed each other, and with the addition of a third point of contact, i.e. the stabilizer pad 21, the stability of the clamp member 15 when it is positioned around the valve stem 3 is greatly enhanced when compared to a two point contact system. The embodiment of FIG. 2 is especially useful in nuclear or hazardous material applications where the valve technician must wear protective clothing when working on the valve, since the clamp member 15 can be easily snapped onto the valve stem 3, where it will remain in a stable position as a result of the spring loading of the sensor pad 20 and stabilizer pad 21. The three points of contact also provide for stability of the clamp member 15 during operation of the valve.

A sensor 24 is provided at the end of the semi-circular clamping member 15 proximate the sensor pad 20. The sensor 24 preferably senses the relative distance between the sensor 24 and the valve stem 3 directly, or alternatively, senses the relative distance between the sensor 24 and the sensor pad 20. Any diametral change in the valve stem 3 is thereby detected by the sensor 24, since the diameter of the valve stem 3 is held stationary relative to the clamping member 15 by the reference pad 17. The sensor 24 can be positioned directly behind the sensor pad 20 in order to sense the opposed surface of the sensor pad 20, or a cut-out can be provided in the sensor pad 20 to permit the sensor 24 to detect the valve stem 3 directly. Diametral change in the valve stem 3 is transmitted as an electrical signal through electrical cable 9 to the signal conditioning module 10 and to the data recording device 11 and the computing and display device 12. The sensor pad 20 is provided with a spring mechanism 25 of a lower spring rate than the semi-circular clamp member 15 itself so that all diametral changes in the cylindrical member or valve stem 3 are realized at the sensor 24 and changes in the stability, shape or size of the semi-circular clamp member 15 have an insignificant effect on the measuring capabilities of the sensor 24.

In this embodiment, the sensor 24 is a linear capacitive reactance sensor, that is able to generate electrical signals indicating small relative movements of the valve stem 3 on sensor pad 20 by threading into an opening in the end of the semi-circular clamping member 15, as best illustrated in FIG. 2. Other types of sensors 24, such as an eddy current or Hall-effect probe, a linear variable differential transformer, a laser or other optical sensor, an ultrasonic sensor, or a strain gage displacement transmitter, could also be used so long as the sensor 24 is able to accurately and reliably detect very small diametral changes in the valve stem 3 and produce an electrical signal representative of such diametral changes. For this embodiment, a Model No. HPT-40 linear capacitive reactance sensor manufactured and sold by Capacitec, Ayer, Mass. was used and gave good results.

The diametral extensometer of this invention, unlike previous diametral extensometers, does not use the clamping member 15 itself to receive the diametral change strains, but rather all such strains are transmitted directly from the valve stem 3 to the sensor 24.

If desired, the sensor 24 should be able to be easily installed in and removed from the clamping member 15 so that defective sensors could be easily replaced or allow for a single sensor 24 to be used with several clamping members 15, each of which is designed to fit a different size or type of valve stem 3. The electrical signals generated by the sensor 24 corresponding to the diametral changes of the valve stem 3 under various operation conditions can be stored in the data recording device for further analysis and used to compute the true axial forces acting on the valve stem 3 by the computing and display device 12, such as a personal computer, using Hooke's Law and Poisson's ratio for the valve stem material.

Figure 4:
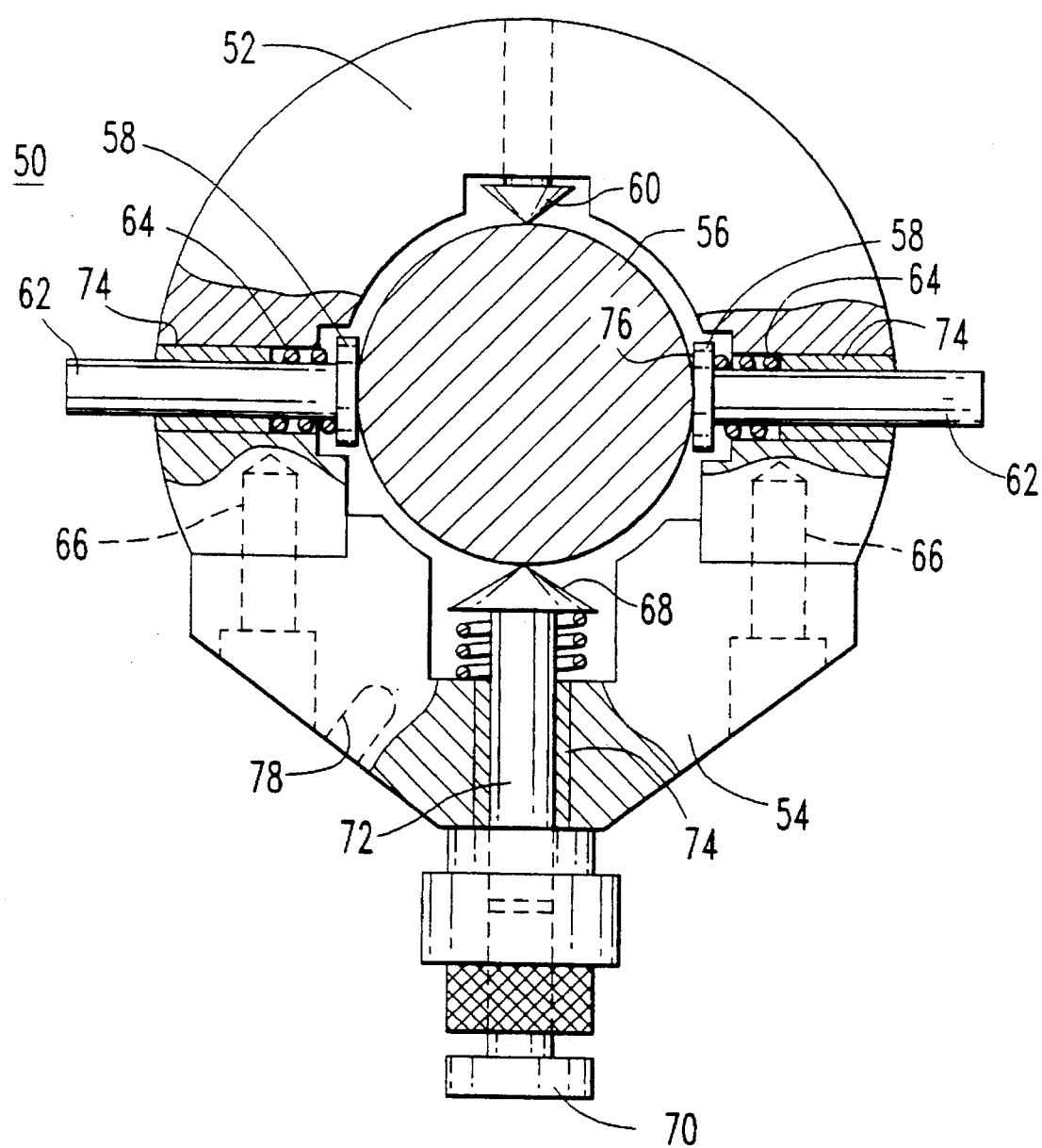
FIG. 4 is a top view of an embodiment of the diametral extensometer utilizing a two-piece clamp member and a four-point contact system.

FIG. 4 illustrates another embodiment of a diametral extensometer 50 of this invention, having a first clamp member 52 and a second clamp member 54. First clamp member 52 is adapted to fit around and to be space from the outer periphery of a valve stem 56 or other load carrying member. Stabilizer pads 58 are spring mounted at opposing ends of the first clamp member 52, and are adapted to be biased against the valve stem 56 when the first clamp member 52 is positioned on the valve stem 56. A reference pad 60 is attached to the first clamp member 52 at a position between the two stabilizer pads 58, and is adapted to make contact with the valve stem 56 when the first clamp member 52 is positioned on the valve stem 56. Stabilizer pads 58 may have extensions 62 which extend beyond the first clamp member 52 so that the stabilizer pads 58 can easily be retracted against the biasing springs 64 to facilitate the positioning of the first clamp member 52 onto the valve stem 56. In this manner, first clamp member 52 becomes self-supporting on the valve stem 56 with three points of contact for stability, thereby simplifying the installation of the second clamp member 54 which is connected to the first clamp member 52 by connectors 66. Connectors 66 may be screws, or bolts, or preferably a type of quick-disconnect connector such as a spring clip, snap connection or twist connector for ease of installation and removal in nuclear and hazardous environments. A sensor pad 68 is spring mounted to the second clamp member 54 in a position generally opposite from the reference pad 60. Once assembled onto a valve stem 56, the diametral extensometer 50 provides a very stable, four-point contact platform for the measurement of changes in the diameter of valve stem 56. The use of four points of contact facilitates the installation of this device on threaded shafts because it improves the stability of the device. The use of four mounting points also reduces the risk of the extensometer moving in relation to the shaft as the valve stem 56 is stroked, thereby providing a more accurate, field ready device. Reference pad 60 and sensor pad 68 may be adapted to make point contact with the valve stem 56, thereby eliminating any possibility of error in measurement resulting for a rocking motion of these pads.

A sensor 70 is mounted to the second clamp member 54 and is operable to detect and to signal relative movement between the second clamp member 54 and an extension 72 attached to the sensor pad 68, thereby providing a measurement of changes in the diameter of the valve stem 56. Sensor 70 and sensor pad 68 may be adapted to permit the sensor 70 to project through or past the sensor pad 68, thereby permitting sensor 70 to sense the valve stem 56 directly. Sensor 70 may be mounted in a fine-threaded connection to facilitate precise adjustment of its zero position. Sensor 70 may be any of the several types of sensors discussed above, such as a capacitive reactance sensor. The output from sensor 70 is connected to appropriate signal processing devices for determining the change in diameter of the valve stem 56, and for calculation of the associated loads being placed upon the stem 56. Because the operation and/or accuracy of certain types of sensors may be affected by static electricity or grounding effects, a connection 78 is provided for a grounding circuit.

In order to ensure smooth operation of this device, it is important to minimize friction between moving parts, since the magnitude of the strains involved in very small, and any friction may cause the parts to move in a non-linear fashion, thereby introducing error into the measurement of the forces acting on the valve stem 56. A non-stick bearing material 74, such as Teflon (trademark) or a graphite impregnated metal, may be inserted between the clamp members 52,54 and the pad extensions 62,72. Furthermore, the surface 76 of stabilizer pad 58 which is in contact with the valve stem 56 can be made to be a non-stick surface to reduce the loads induced into the stabilizer pads 58.

It is believed that the present invention and its advantages will be understood from the above description and the accompanying drawings, and it will be apparent that changes may be made in the form, construction and arrangement as described without departing from the scope of this invention.

We claim:

1. A device for determining the diametral changes in a shaft produced by axial loads on said shaft, comprising:

a first clamp member adapted to be spaced from and to partially surround the outer periphery of said shaft;

a first stabilizer pad springably attached to a first end of said first clamp member and adapted to be biased against said shaft;

a second stabilizer pad springably attached to a second end of said first clamp member and adapted to be biased against said shaft opposed said first stabilizer pad;

a reference pad fixably attached to said first clamp member between said first stabilizer pad and said second stabilizer pad and adapted to make contact with said shaft;

a second clamp member attached to said first clamp member and adapted to be spaced from and to partially surround the outer periphery of said shaft;

a sensor pad springably attached to said second clamp member opposed said reference pad and adapted to be biased against said shaft;

means for sensing relative movement between said second clamp member and said sensor pad.

2. The device of claim 1, wherein said first clamp member and said second clamp member are attached by a means for quick-disconnecting.

3. The device of claim 1, wherein said reference pad and said sensor pad are adapted to make essentially point contact with said shaft.

4. The device of claim 1, wherein the surface of said first stabilizer pad which is adapted to make contact with said shaft comprises a non-stick surface.

5. The device of claim 1, further comprising a non-stick bearing material disposed between said first stabilizer pad and said first clamp member.

6. The device of claim 1, further comprising a non-stick bearing material disposed between said sensor pad and said second clamp member.

7. The device of claim 1, further comprising a means for determining the axial loads acting on said shaft connected to said means for sensing.

8. The device of claim 1, further comprising a computing and display device connected to said means for sensing.

* * * * *